United States Patent [19]
Totakura et al.

[11] Patent Number: 5,584,857
[45] Date of Patent: Dec. 17, 1996

[54] SUTURE COATING AND TUBING FLUID

[75] Inventors: Nagabhushanam Totakura, North Haven, Conn.; Shalaby W. Shalaby, Anderson, S.C.; Lyudmila Kokish, Orange, Conn.

[73] Assignee: United States Surgical Corporation, Norwalk, Conn.

[21] Appl. No.: 338,404

[22] Filed: Nov. 14, 1994

[51] Int. Cl.$^6$ ................................................. A61B 17/04
[52] U.S. Cl. ............................ 606/228; 606/229; 606/230
[58] Field of Search ...................................... 606/228–231

[56] References Cited

U.S. PATENT DOCUMENTS

| | | |
|---|---|---|
| 1,239,690 | 9/1917 | Hollister . |
| 2,128,701 | 8/1938 | Gelinsky . |
| 2,394,054 | 3/1941 | Hall . |
| 2,519,404 | 8/1950 | Rynkiewicz . |
| 2,524,772 | 10/1950 | Davis . |
| 2,576,576 | 11/1951 | Cresswell . |
| 2,640,752 | 6/1953 | Davis et al. . |
| 2,694,487 | 11/1954 | Powers . |
| 3,166,073 | 1/1965 | Kronenthal . |
| 3,413,079 | 11/1968 | Rich . |
| 3,478,140 | 11/1969 | Kronenthal et al. . |
| 3,773,737 | 11/1973 | Goodman . |
| 3,896,814 | 7/1975 | Vivien et al. . |
| 3,942,532 | 3/1976 | Hunter et al. . |
| 4,027,676 | 6/1977 | Mattei . |
| 4,105,034 | 8/1978 | Shalaby et al. . |
| 4,185,637 | 1/1980 | Mattei . |
| 4,190,720 | 2/1980 | Shalaby . |
| 4,201,216 | 5/1980 | Mattei . |
| 4,347,234 | 8/1982 | Wahlig et al. . |
| 4,506,672 | 3/1985 | Bichon . |
| 4,532,929 | 8/1985 | Mattei et al. . |
| 4,624,256 | 11/1986 | Messier et al. . |
| 4,649,920 | 3/1987 | Rhum . |
| 4,788,979 | 12/1988 | Jarrett et al. . |
| 4,791,929 | 12/1988 | Jarrett et al. . |
| 4,994,074 | 2/1991 | Bezwada et al. . |
| 5,104,398 | 4/1992 | Planck et al. . |

FOREIGN PATENT DOCUMENTS 5735080  2/1987  Japan .

*Primary Examiner*—Gary Jackson

[57] ABSTRACT

A coating and tubing fluid for sutures, especially gut sutures, is provided. The coating composition includes linseed oil, an organic solvent and a catalyst. The tubing fluid includes water, a softening agent, a $C_2$–$C_4$ alcohol and a lubricant of fatty acids, fatty acid alcohols and/or triglycerides of fatty acids. Gut sutures coated with the coating composition may be stored or packaged in the tubing fluid to provide sutures with improved flexibility, pliability, run-down performance and superior resistance to fraying and breaking.

3 Claims, 1 Drawing Sheet

SUTURE COATING AND TUBING FLUID

BACKGROUND

1. Technical Field

The present disclosure relates to surgical sutures and more particularly to coatings for sutures and fluids in which sutures are stored and/or packaged.

2. Background of Related Art

Absorbable sutures are manufactured from natural or synthetic materials. Some of the earliest absorbable sutures were made of collagenous material taken from sheep intestines. Such sutures are still in use today and are commonly referred to as catgut or gut sutures or ligatures. In the present specification, gut suture refers to a collagen based suture or ligature of any type or origin. Gut sutures may be prepared in the form of threads or strands that are undesirably stiff before subsequent treatment which renders them flexible or pliable. Flexibility and pliability are important to allow efficient manipulation of the suture by the surgeon during an operation.

A suture having a good degree of flexibility and pliability can conform closely to body tissue without undue pressure. Good flexibility and pliability enhance the degree to which a suture can be tied down, knotted and securely placed in a desired position.

Various attempts have been made to modify and optimize the physical characteristics of gut sutures. For example, tubing fluids are liquids which are used to condition gut sutures to achieve or enhance flexibility and pliability. Tubing fluids are also used to preserve gut sutures. Tubing fluids typically contain an alcohol such as isopropyl alcohol and a relatively small percentage of water. Examples of tubing fluids are found in U.S. Pat. Nos. 1,239,690, 2,394,054, 2,519,404, 2,524,772, and 2,694,487. Ideally, the tubing fluid aids the gut suture to retain its flexibility and pliability without adversely affecting the strength and overall integrity of the suture.

Commercially available gut sutures are immersed in tubing fluid, sterilized and supplied to surgeons in packages or tubes which contain tubing fluid (hence the name tubing fluids). The alcohol and water keep the suture flexible and pliable as long as they remain in contact with the suture. As the tubing fluid evaporates, the suture loses its flexibility and pliability which may affect handling characteristics.

In addition to tubing fluids, various suture coatings which adhere to the surface of the suture have been developed in an attempt to maintain flexibility and control swelling and fraying. Such coatings are also intended to improve the handling characteristics of sutures and maximize run-down performance. For example, lubricants which are employed to permit slippage between collagen filaments of a multifilament thread or strand are described in U.S. Pat. No. 2,576,576. Such lubricants include fatty oils such as polyhydric alcoholesters of such fatty acids as stearic acid, oleic acid, linoleic acid, and myristic acid. U.S. Pat. No. 3,478,140 is directed to applying a solution of dehydrated castor oil in hexane or an emulsion of dehydrated castor oil to reconstituted collagen strands and then drying the strands under heat and tension for surface coating. Another castor oil containing emulsion which is dried onto collagen sutures is described in U.S. Pat. No. 3,413,079. Yet another coating composition containing castor oil is described in U.S. Pat. No. 4,027,676. In U.S. Pat. No. 4,185,637, a composition containing a gel of a fatty acid salt such as calcium stearate is described as being deposited on the surface of a suture by solvent evaporation to form a coating. Sutures which have been treated with a coating lubricant containing stearic acid or calcium stearate are compared in U.S. Pat. No. 4,201,216. The stearic acid lubricant has a much lower tie-down rating than calcium stearate lubricant.

SUMMARY

Sutures, especially gut sutures, are coated with a composition containing from about 2% by weight to about 40% by weight of linseed oil to improve pliability, flexibility and resistance to fraying. The coating composition includes an organic solvent such as toluene, xylene or benzene, etc. The coating composition also includes a metal salt of a $C_5$–$C_{15}$ saturated monocarboxylic acid such as a manganese salt of hexanoic acid, or the manganese salt of naphthanoic acid, commercially available from OM Group (Cleveland, Ohio) as 6% Manganese HEX-CEM and 6% Manganese NAP-ALL, respectively. Other metals suitable for use in the metal salts of hexanoic acid and/or naphthanoic acid include cobalt, calcium, bismuth, nickel, zinc, zirconium, iron, and lead. The present disclosure encompasses the above-described coating composition, sutures coated with the coating composition and methods of coating a suture with the coating composition.

Additionally, a tubing fluid for storing or packaging the coated sutures described above, is disclosed which includes water, a softening agent, a $C_2$–$C_4$ alcohol and a lubricant of at least one fatty acid such as stearic acid, lauric acid, myristic acid, palmitic acid, oleic acid, linoleic acid and their corresponding alcohols; and/or fatty acid triglycerides, such as castor oil. The softening agent is preferably triethanolamine and the alcohol is preferably isopropyl alcohol. The tubing fluid has a water content of from about 4% by weight to about 15% by weight, a softening agent content of from about 0.75% by weight to about 2% by weight, a $C_2$–$C_4$ alcohol content of about 80% by weight to about 94% by weight and a lubricant content of about 1% by weight to about 10% by weight. A suture package includes a container having the coated sutures therein which are in contact with the tubing fluid. Contacting the coated sutures, with the robing fluid enhances and preserves the sutures.

In another aspect, a suture fraying resistance test system and method of testing the fraying resistance of sutures are provided. In accordance with this aspect, a movable dynamic suture is placed in contact with a static or stationary suture. One end of the dynamic suture is attached to a vertically moveable grip and the other end is attached to a weight. The grip and the weight are capable of vertical movement such that the dynamic suture rubs against the static suture. The vertical movement of the grip and dynamic suture is continued until one of the sutures breaks due to fraying.

DETAILED DESCRIPTION OF PREFERRED EMBODIMENTS

Figure 1:
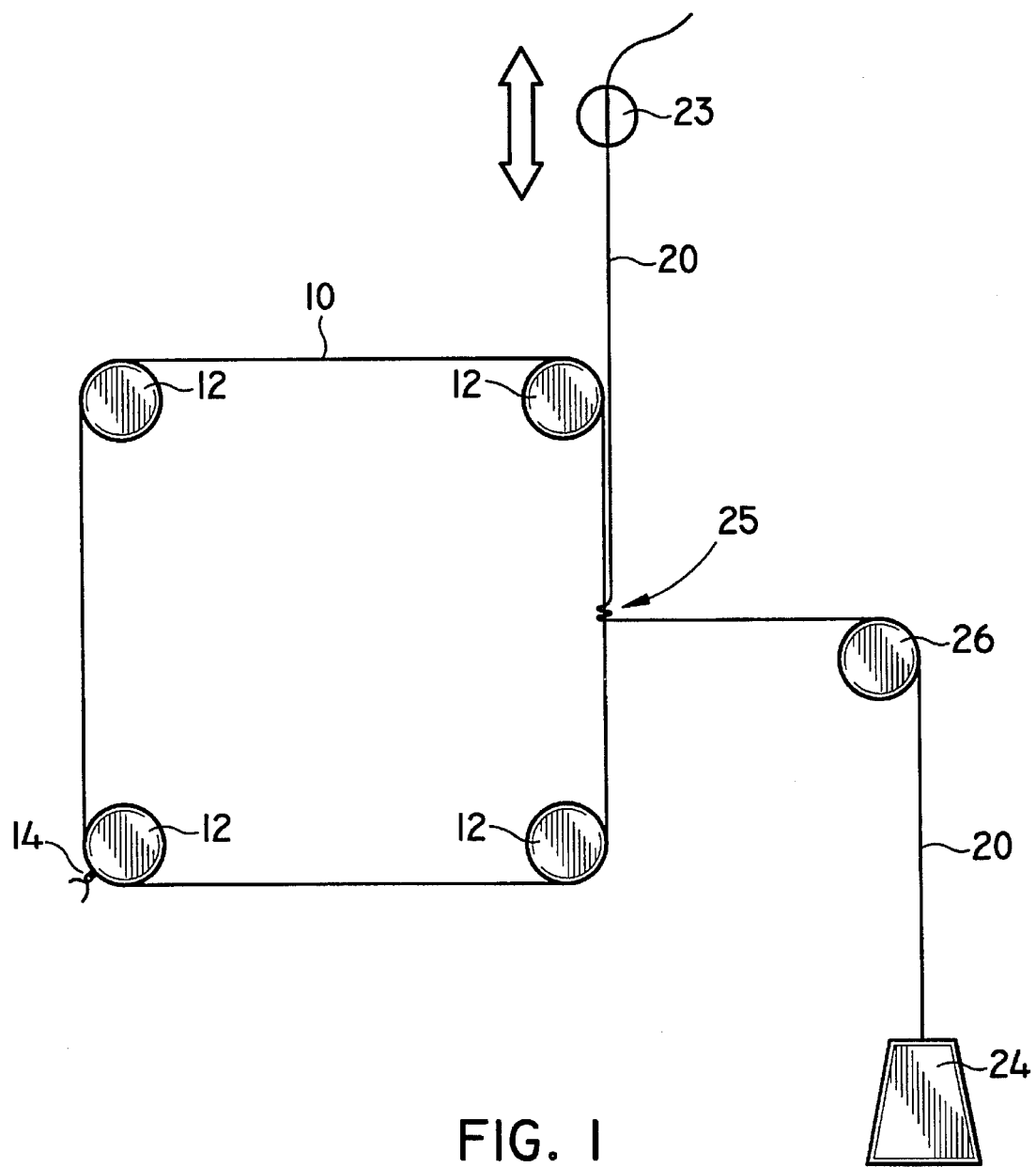
FIG. 1 is a schematic view of a fray testing system.

The suture coating composition described herein increases fraying resistance, improves fiber lubricity and enhances knot run-down characteristics of sutures. The coating composition is easy to apply and adheres nicely to the sutures. Gut sutures are particularly benefited by treatment with the present coating composition which significantly improves surface properties as compared to uncoated gut sutures. The coating softens the surface and covers or fills in surface imperfections.

The coating composition is a liquid and includes linseed oil, an organic solvent and a metal salt of a $C_5$–$C_{15}$ saturated monocarboxylic acid. Linseed oil may be raw, but is more preferably boiled and is present in the composition in an amount ranging from about 2% by volume to about 40% by volume.

The organic solvent is used to lower the viscosity and increase the penetrating characteristics of the composition, i.e., by increasing the amount of solvent the viscosity is lowered. The solvent is volatile and leaves a coating deposited on the suture when it evaporates. Suitable organic solvents include toluene, xylene or benzene, etc. The amount of organic solvent in the composition ranges from about 50% by volume to about 98% by volume, and is preferably about 75% by volume when the coating composition is to be applied to the suture by a dipping operation and about 95% by volume when the coating composition is to be applied to the suture by a spraying composition.

The metallic salt of a $C_5$–$C_{15}$ saturated monocarboxylic acid is present for its catalyst effect. The salt reacts with unsaturated double bonds in linseed oil resulting in polymerization. Suitable metallic salts of $C_5$–$C_{15}$ saturated monocarboxylic acids include a manganese, cobalt, calcium, bismuth, nickel, zinc, zirconium, iron or lead salt of hexanoic acid or such salts of naphanoic acid. The salt content of the coating composition ranges from about 0.1% by volume to about 10% by volume.

The coating composition may be applied to sutures by dipping the suture in a reservoir of coating composition, moving sutures past a brush or applicator wetted with the composition, or by spraying the composition onto sutures. The amount of coating composition may be varied depending on the construction of the sutures, e.g., the number of filaments and tightness of braid or twist. A less viscous composition will penetrate further into the suture than a more viscous composition. In addition, viscosity of the composition is variable pending on the method of application. For example, a preferred dipping composition contains about 25ml raw or boiled linseed oil, about 2ml to about 2.5ml manganese salt of hexanoic acid and about 75ml toluene. A preferred spraying composition contains about 10ml raw or boiled linseed oil, about 0.6ml to about 1 ml manganese salt of hexanoic acid, and about 90ml toluene.

In the case of dip coating, the sutures are immersed in the coating composition for about 5 minutes, tied to a frame and the composition is allowed to dry and cure. If spray coating is utilized, the sutures are mounted on a frame and sprayed with a spray gun which is preferably a light volume, low pressure sprayer. In either case, the temperature for curing ranges from about 40° C. to about 90° C. but is preferably about 70° C. to about 100° C. and curing time ranges from about 6 hours to about 20 hours, but is preferably about 16 hours in air.

Gut sutures that are uncoated or coated with the above-described coating composition or other coating compositions are normally stored and/or packaged prior to use in surgery. The tubing fluid described herein preserves, increases fraying resistance and confers flexibility and pliability to gut sutures stored therein.

The present tubing fluid for storing or packaging sutures includes water, a softening agent, a $C_2$–$C_4$ alcohol and a lubricant of stearic acid and/or castor oil. The water should be sterile and/or pyrogen free and is present in the fluid in an amount ranging from about 4% by weight to about 15% by weight, but preferably about 9% by weight.

The softening agent softens and preserves the gut suture. Suitable softening agents include organic amine compounds such as triethanolamine. The softening agent is present in an amount ranging from about 0.75% by weight to about 2% by weight, but preferably about 1–1.5% by weight of the fluid.

The alcohol component of the tubing fluid is a $C_2$–$C_4$ alcohol, preferably isopropyl alcohol. The alcohol is present in an amount ranging from about 80% by weight to about 94% by weight of the tubing fluid.

Fatty acids such as stearic acid, lauric acid, myristic acid, palmitic acid, oleic acid, linoleic acid and/or their corresponding alcohols; and/or fatty acid triglycerides such as castor oil are liquid lubricants in the tubing fluid with stearic acid and/or castor oil being preferred. The lubricant component is present in the fluid in an amount ranging from about 1% by weight to about 10% by weight, but preferably about 2–5% by weight.

The tubing fluid is effective in enhancing flexibility and pliability of gut sutures without causing undue swelling of the suture. Indeed, as is shown below, resistance to fraying and breaking of the suture is actually increased. The tubing fluid leaves a residue of lubricant over the surface of the suture which slows or prevents evaporation of the components which keep the suture flexible and stipple. In the case of a gut suture which has a surface coating such as that provided by the coating composition above, the tubing provides a second layer or film over the coating to further improve surface qualities.

A fray resistance test was used to compare untreated sutures, sutures treated with coating compositions and tubing fluids as described herein. FIG. 1 schematically diagrams the fray testing system. A static suture 10 is wound around rollers 12 and tied into a knot 14. A dynamic suture 20 is placed into a grip 23 and extended to reach the static suture 10 where it is wrapped twice at point 25 around the static suture 10. The dynamic suture 20 is extended around roller 26 and attached to a weight 24 which supplies tension to the dynamic suture 20. The grip 23 and dynamic suture 20 move up and down to cause the sutures to rub against each other at point 25. One cycle is a complete up and down movement of the grip 23 and dynamic suture 20. Testing conditions included a preload weight which is 15% of the USP limit on average knot pull strength for gut sutures. The travel distance for the grip was 50mm for each cycle at a speed of 500mm/minute. The test is dependent on the number of cycles needed to break a suture due to the fraying which occurs when one strand of suture, under applied load, slides against another static strand. A modified Sintech 1/G MTS system tester is used to conduct the fraying test. The bottom grip is removed from the tester, the load calibrated and gage set to zero. The static suture 10 is tied with sufficient tension around the rollers 12 of the fixture, forming a square. The fixture is adjusted so the point 25 where the static suture 10 and dynamic suture 20 interface is in line with the center line of the upper grip. Table I shows preload weight for the fraying resistance test. The test is initiated with cycling observed until one of the sutures breaks to stop the test. If strands should lock themselves in a knot and do not slide against each other it is considered a break. The average number of cycles ($X_{ave.}$) is $X_{ave.}=(X_1+X_2+\ldots+X_n)/n$ wherein $X_n$ is the number of cycles to break each pair of strands and n is the number of pairs. The standard deviation $\overline{S}$ is calculated as $$\bar{S} = \sqrt{\frac{\Sigma(x_1 - x)^2}{n - 1}}$$

TABLE I

Preload weights for Fray resistance test

| | | Gut Sutures | |
|---|---|---|---|
| Sizes | Dia., mm | USP Knot pull kg | Preload weights. 15% of USP Knot pull, kg. |
| 9/0 | 0.040–0.049 | — | — |
| 8/0 | 0.050–0.069 | 0.045 | 0.007 |
| 7/0 | 0.070–0.099 | 0.07 | 0.01 |
| 6/0 | 0.10–0.149 | 0.18 | 0.03 |
| 5/0 | 0.15–0.199 | 0.38 | 0.06 |
| 4/0 | 0.20–0.249 | 0.77 | 0.12 |
| 3/0 | 0.30–0.339 | 1.25 | 0.2 |
| 2/0 | 0.35–0.399 | 2.00 | 0.3 |
| 0 | 0.40–0.499 | 2.77 | 0.42 |
| 1 | 0.50–0.599 | 3.80 | 0.55 |
| 2 | 0.60–0.699 | 4.51 | 0.7 |

The following examples should be considered as illustrative and not as limitations of the present description. The examples show illustrative formulations and superiority of the present coating composition and tubing fluid in enhancing properties of gut sutures.

EXAMPLE I

A coating composition was made by mixing 25ml boiled linseed oil with 75ml toluene and 2.05ml manganese salt of hexanoic acid in an erlenmeyer flask for about 30 minutes at ambient temperature until a uniform mixture was obtained. Size 1 chrome gut suture was immersed in the coating composition for 5 minutes, removed and tied onto a metallic frame and cured at 70° C. for 16 hours in air.

EXAMPLE II

A coating composition was made by mixing 5ml raw linseed oil with 95ml toluene and 0.6ml manganese salt of hexanoic acid in an erlenmeyer flask for about 30 minutes at ambient temperature until a uniform mixture was obtained. Size 1 chrome gut suture was tied onto a metal frame and the coating solution was sprayed on using light volume, low pressure spray equipment available from Wagner Company, Model HVLP. The coating was allowed to cure for 16 hours in air at 70° C.

EXAMPLE III

A tubing fluid was made by mixing 7 gms pyrogen free water with 1.4 gms triethanolamine and 91.6 gms isopropyl alcohol. 97ml of the resulting mixture were well mixed with 3ml (2.88 gms) castor oil to form a tubing fluid.

EXAMPLE IV

A tubing fluid was made by mixing 9 gms pyrogen free water with 1.4 gms triethanolamine and 89.6 gms isopropyl alcohol. 97ml of the resulting mixture were well mixed with 3ml (2.88 gms) castor oil to form a tubing fluid.

EXAMPLE V

A tubing fluid was made by mixing 12 gms pyrogen free water with 1.4 gms triethanolamine and 86.6 gms isopropyl alcohol. 97ml of the resulting mixture were well mixed with 3ml (2.88 gms) castor oil to form a tubing fluid.

EXAMPLE VI

A tubing fluid was made by mixing 9 gms pyrogen free water with 1.4 gms triethanolamine and 89.6 gms isopropyl alcohol. 96 ml of the resulting mixture were well mixed with 4ml (3.84 gms) castor oil to form a tubing fluid.

EXAMPLE VII

A tubing fluid was made by mixing 9.0 gms pyrogen free water with 1.4 gms triethanolamine and 89.6 gms isopropyl alcohol. 47 ml of the resulting mixture were well mixed with 3 gms stearic acid to form a tubing solution. Chrome size 1 gut suture was stored in the tubing fluid for a minimum of 4 hours and tested for the number of cycles to break. The number of cycles needed to break was 56.1 with a standard deviation of 26.6.

EXAMPLE VIII

Coated sutures from Example VII were wet for about 20 seconds in distilled water and tested for number of cycles to break. The number of cycles needed to break was 2.4 with a standard deviation of 0.7.

COMPARATIVE EXAMPLE I

A coating solution was made by mixing 5ml castor oil with 95ml toluene and 0.5ml manganese salt of hexanoic acid in an erlenmeyer flask for about 30 minutes at ambient temperature until a uniform mixture was obtained. Size 1 chrome gut suture was tied onto a metal frame and sprayed with the coating solution using light volume, low pressure spray equipment available from Wagner Company, Model HVLP. The coating was allowed to cure for 16 hours in air at 70° C.

COMPARATIVE EXAMPLE II

A coating solution was made by mixing 10ml castor oil with 90ml toluene and 1.0ml manganese salt of hexanoic acid in an erlenmeyer flask for about 30 minutes at ambient temperature until a uniform mixture was obtained. Size 1 chrome gut suture was tied onto a metal frame and sprayed with coating solution using light volume, low pressure spray equipment available from Wagner Company, Model HVLP. The coating was allowed to cure for 16 hours in air at 70° C.

Table II below indicates the effect of tubing fluid having 3% castor oil in comparison to tubing fluid without castor oil on tensile and fraying properties of Size 1 chrome gut sutures.

TABLE II

Effect of Water Concentration and Castor Oil in Packaging Fluids on Tensile and Fraying Properties

| | Non-Sterile Uncoated Gut Suture % Water in the Fluid by Weight without Castor Oil | | |
|---|---|---|---|
| | 7% (See Example III) | 9% (See Example IV) | 12% (See Example V) |
| Diameter of Packaged Suture mm | 0.516 | 0.525 | 0.541 |
| Tensile Kg. | 12.42 | 11.68 | 10.27 |
| | (1.07)* | (0.69) | (0.55) |
| Modulus Kpsi | 351 | 374 | 279 |
| "Fraying" Out of Package Data Cycles to Break | 0.3 | 3.4 | 1.7 |
| | (0.1) | (2.3) | (0.8) |
| Fraying "Pre-Wetting" Suture Data Wet/iml Pre-Wetting Time | | | |
| 20 sec | 1.4 | 1.4 | 1.4 |
| | (0.0) | (0.1) | (0.0) |
| 60 sec | 1.3 | 1.4 | 1.0 |
| | (0.0) | (0.5) | (0.8) |

| | Sterile Ethicon Chromic Gut Size 1 Sutures out of package | Non-Sterile Sutures with 3% Castor Oil in the Fluid | | |
|---|---|---|---|---|
| | | (Example III) | (Example IV) | (Example V) |
| Diameter of Packaged Suture mm | 0.554 | 0.534 | 0.5512 | 0.5413 |
| Tensile Kg. | 8.9 | 11.25 | 9.4 | 10.39 |
| | (0.772) | (0.93) | (1.62) | (0.24) |
| Modulas Kpsi | 301.46 | 422.8 | 309.5 | 299.4 |
| "Fraying" Out of Package Data Cycles to Break | 8.8 | 9.8 | 8.9 | 7.1 |
| | (2.2) | (4.7) | (2.3) | (1.8) |
| Fraying "Pre-Wetting" Suture Data Wet/iml Pre-Wetting Time | | | | |
| 20 sec | 1.4 | 18.9 | 3.4 | 3.7 |
| | (0.1) | (9.7) | (2.3) | (2.8) |
| 60 sec | 1.4 | 3.1 | 2.3 | 2.6 |
| | (0.8) | (2.4) | (1.5) | (0.7) |

*Standard Deviation ( )

Table III below indicates the effect size 1 chrome gut sutures coated with the present coating composition and stored in the indicated tubing fluids.

TABLE III

Effect of Coating Composition and Tubing Fluid on Non-Sterile Size 1 Chrome Gut Suture

| | Fraying, # of Cycles to Break | | | | | |
|---|---|---|---|---|---|---|
| | | | Prewetting for | | | |
| Suture Packaging Data | Suture out of Package | | 20 Sec | | 60 Sec | |
| 1. Linseed Oil Coating composition (Applied 25% Boiled Oil Solution in Toluene per Example I Tubing fluid without castor oil, see Example IV) | 5.5 | (1.0)* | | | | |
| 1A. Same as #1 + 4% Caster Oil in the Tubing Fluid per Example VI | 14.3 | (1.8) | 11.8† | (6.1) | 6.8† | (5.1) |
| 2. Castor Oil Coating** (Applied as %5 Solution in Toluene per Comparative Example I) | 2.8 | (2.8) | 1.4 | (0.10) | | |
| 2A. Same as #2 + 3% Castor Oil in the fluid per Example IV | 8.5 | (1.9) | 2.0 | (0.6) | | |
| 3. Castor Oil Coating (Applied as 10% Solution in Toluene per Comparative Example II) | 2.8 | (2.5) | 1.7 | (0.5) | | |
| 3A. Same as #3 + 3% Castor Oil in the Fluid per Example IV | 5.9 | (2.6) | 1.5 | (0.0) | | |
| 4. 3% Castor Oil only in the Fluid per | 8.9 | (2.3) | 3.4 | (2.3) | | |

TABLE III-continued

Effect of Coating Composition and Tubing Fluid on Non-Sterile Size 1 Chrome Gut Suture

| | Fraying, # of Cycles to Break | | | | | |
|---|---|---|---|---|---|---|
| | | | Prewetting for | | | |
| Suture Packaging Data | Suture out of Package | | 20 Sec | | 60 Sec | |
| Example IV | | | | | | |
| 5. Ethicon Chromic Gut Size 1 Suture | 8.8 | (2.2) | 1.4 | (0.1) | 1.4 | (0.8) |

*Standard Deviation in ( )
**Coating was tacky
†Water in the Fluid was 12% and Castor Oil Content 4%, with linseed oil precoated sutures.

Table IV shows the fray resistance of uncoated and coated size 1 chrome gut sutures and effect of tubing fluid.

TABLE IV

Fray resistance of Size 1 Chromic Gut sutures.

| Suture Sample | Cycles to break | Average | Standard deviation |
|---|---|---|---|
| control No coating, cured 16 hr at 100 C. | 1, 1, 1, 1, 1 | 1 | 0 |
| 25% lin. oil in tol. per Example I but cured for 16 hr at 100 C. | 7, 8, 8, 8, 10 | 8 | 1.1 |
| 25% lin. oil in tol. per Example I but cured for 16 hr at 100 C. 4% cast. oil tubing fluid per Example VII | 17, 20, 27, 16, 18 | 20 | 4.4 |

As can be seen from the above examples and tests, the coating compositions containing linseed oil clearly improved the properties of gut sutures. The fraying test showed that a 25% boiled linseed oil coating composition on gut sutures increased the number of cycles to break from 3.4 (Table II) to 5.5 (Table III). The coating covered any imperfections and softened the surface as well. The number of cycles to break showed significant improved when a tubing fluid according to the present description is used. The uncoated no castor oil 9% water tubing fluid took In another aspect of the tests, the effect of prewetting was determined. As is shown in Table III, sutures were removed from the tubing fluid, soaked in water for 20 or 60 seconds and then tested for fraying. The results show that the commercially available Ethicon suture lost its lubricating property in 20 seconds with a value of 1.4 cycles to break. The linseed oil coated sutures stored in castor oil 9% water tubing fluid took 11.8 cycles to break after 20 seconds prewetting and 6.8 cycles after 60 seconds prewetting.

It will be understood that various modifications may be made to the embodiments disclosed herein. Therefore, the above description should not be construed as limiting, but merely as exemplifications within the scope and spirit of the claims appended hereto.

What is claimed is:

1. A suture having a coating, the coating comprising linseed oil, an organic solvent and a metal salt of a $C_5$–$C_{15}$ saturated monocarboxylic acid, wherein the organic solvent is selected from the group consisting of toluene, xylene, and benzene and the metal salt of $C_5$–$C_{15}$ saturated monocarboxylic acid is selected from the group consisting of manganese salt of hexanoic acid, cobalt salt of hexanoic acid, calcium salt of hexanoic acid, bismuth salt of hexanoic acid, nickel salt of hexanoic acid, zinc salt of hexanoic acid, zirconium salt of hexanoic acid, iron salt of hexanoic acid, lead salt of hexanoic acid, manganese salt of naphthenic acid, cobalt salt of naphthenic acid, calcium salt of naphthenic acid, bismuth salt of naphthenic acid, nickel salt of naphthenic acid, zinc salt of naphthenic acid, zirconium salt of naphthenic acid, iron salt of naphthenic acid, and lead salt of naphthenic acid.

2. Suture having a coating according to claim 1, wherein the coating contains from about 2% by weight to about 40% by weight of linseed oil.

3. A suture having a coating according to claim 1, wherein the suture is made of collagen.

\* \* \* \* \*